United States Patent [19]

Delfosse

[11] Patent Number: 5,658,341
[45] Date of Patent: Aug. 19, 1997

[54] TIBIAL IMPLANT FOR A KNEE PROSTHESIS

[75] Inventor: Jacques Delfosse, Nancy, France

[73] Assignee: Medinov S.A., Roanne, France

[21] Appl. No.: 331,521

[22] PCT Filed: Mar. 9, 1994

[86] PCT No.: PCT/FR94/00260

§ 371 Date: Jan. 9, 1995

§ 102(e) Date: Jan. 9, 1995

[87] PCT Pub. No.: WO94/20047

PCT Pub. Date: Sep. 15, 1994

[30] Foreign Application Priority Data

Mar. 10, 1993 [FR] France .................. 93 03034

[51] Int. Cl.$^6$ .................................................. A61F 2/38
[52] U.S. Cl. ............................................................ 623/20
[58] Field of Search ................................. 623/16, 18, 19, 623/20, 22, 23

[56] References Cited

U.S. PATENT DOCUMENTS

| | | | |
|---|---|---|---|
| 4,822,362 | 4/1989 | Walker et al. | 623/20 |
| 4,944,757 | 7/1990 | Martinez et al. | 623/20 |
| 5,062,852 | 11/1991 | Dorr et al. | 623/20 |
| 5,152,797 | 10/1992 | Lockman et al. | 623/20 |
| 5,246,459 | 9/1993 | Elias | 623/20 |
| 5,330,535 | 7/1994 | Moser et al. | 623/20 |
| 5,387,241 | 2/1995 | Hayes | 623/20 |
| 5,413,605 | 5/1995 | Ashby et al. | 623/20 |

FOREIGN PATENT DOCUMENTS

| | | | |
|---|---|---|---|
| 2076838 | 10/1971 | France | 623/20 |
| 2653992 | 5/1991 | France | 623/20 |

*Primary Examiner*—Debra S. Brittingham
*Attorney, Agent, or Firm*—Eckert Seamans Cherin & Mellott

[57] ABSTRACT

A tibial implant for knee prosthesis has a tibial socket (1) accepting a tibial plate (2) notably in polyethylene. The tibial socket (1) has a recess (1a) with a shape and section chosen to allow, from the upper face of said socket (1), the engagement, centering and holding in place, with the capability of angular orientation, of an anchoring and/or stabilizing pin with fins (3).

6 Claims, 4 Drawing Sheets

TIBIAL IMPLANT FOR A KNEE PROSTHESIS

The invention relates to a sliding tricompartmental knee prosthesis.

In a well-known manner, this type of prosthesis essentially comprises a femoral implant and a tibial implant. The invention specifically relates to a tibial implant of the type comprising a metallic socket accepting a polyethylene plate suitably shaped to receive, on sliding, the condyles of the femur.

The tibial sockets on known devices have a stabilizing and/or anchoring pin intended to be impacted in the spongy substance of the proximal extremity of the tibia. These pins are firmly attached, directly or indirectly, to the tibial socket and can have stabilizing fins acting as anti-rotatory devices.

Indirectly attached pins are usually fixed by means of screws under the tibial socket. For example, reference can be made to French Patent Nos. 9,103,595 and 9,109,247 and U.S. Pat. Nos. 4,938,769 and 4,944,757.

In each of the above referenced patents, the stabilizing and/or anchoring pin is supported against the lower face of the tibial socket, while one or more screws are inserted from the upper face of the tibial socket into corresponding fittings in the pin. In some cases, the pin can have a centering head inserted in an opening in the tibial socket. For example, see French patent 9,109,247 and U.S. Pat. No. 4,944,757.

However, it is still necessary in the previously known devices to insert the pin from the underside of the socket and then to fix it in place from above.

It is therefore evident that in all of these previously known devices that the fixing in place of the pin is performed from the underside of the tibial socket in such a way that it is necessary to firmly attach the pin to the socket before its impaction.

Given that it is the pin which determines the positioning of the socket relative to the proximal extremity of the tibia, such previously used arrangements are not rational in that they do not provide appropriate regard for the quality of the fixing of the device in the patient.

The object of the invention is to remedy these drawbacks in a simple, sure, effective and rational manner. Namely, the current invention allows for the impaction of the tibial socket in the leg of a patient prior to the introduction of an optional stabilizing and/or anchoring pin. This allows for a final fitting of the device in the patient rather than before the impaction process begins, as was previously known.

Under the current invention, a tibial socket has been conceived and developed. The tibial socket has a recess and a protuberance jutting out from a lower face of the tibial socket. The protuberance being shaped to act as a pre-anchoring pin to aid in the impaction of the tibial socket. This tibial socket also has a recess of a given shape and section such that the engagement, centering and securing of a stabilizing and/or anchoring pin can be accomplished through an upper face of the tibial socket. Furthermore, the stabilizing and/or anchoring pin optionally has fins and is capable of angular orientation within the tibial socket.

Advantageously, the protuberance jutting out from the lower face of the tibial socket has a flattened cone-shaped external surface.

To ensure that the stabilizing and/or anchoring pin can be locked securely in place, the pin has a head with a shoulder that cooperates with a counterboring in the recess in the tibial socket. Such cooperation allows for the securing of the pin taking into account its insertion from the upper face of the tibial socket. Both the head and the recess cooperating with the head are generally in circular form.

The fins on the stabilizing and/or anchoring pin ensure the rotatory stability of the tibial implant. The fins communicate with traversing slits in the recess of the tibial socket whose number and orientation correspond to the number and orientation of the fins on the pin.

According to a further aspect of the invention, the head of the stabilizing and/or anchoring pin has fittings for fixing to the recess. The fittings comprise vertical slits formed around the periphery of the head for its diametric expansion under the action of a tightening screw.

To ensure the fixing of the tibial socket to the spongy and/or peripheral cortical bone of the tibia, the tibial socket has holes for the passage of the fixing screws. Thus, the tibial socket may be fixed whether or not fitted with the stabilizing and/or anchoring pin.

The tibial socket is asymmetric and has a peripheral rim. The peripheral rim is equipped to facilitate the fixing of a polyethylene tibial plate such that the proper positioning of the tibial plate can be effected after the fixing of the socket.

The invention is described below in more detail with reference being made to the accompanying Figures.

Figure 1:
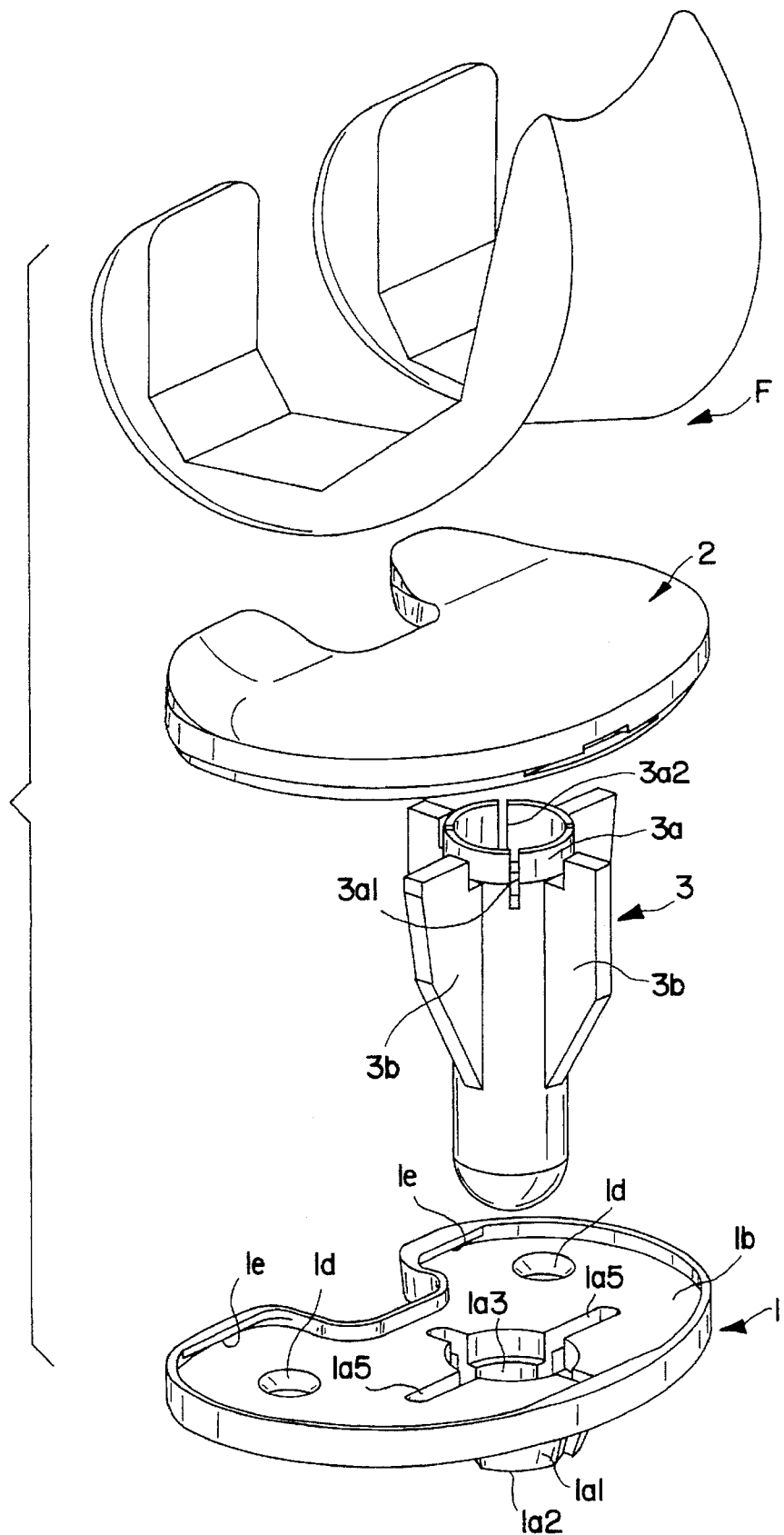
FIG. 1 is a perspective view showing the main elements of the tibial implant, which are shown aligned in order of assembly, an example of a femoral implant is also shown.
Figure 2:
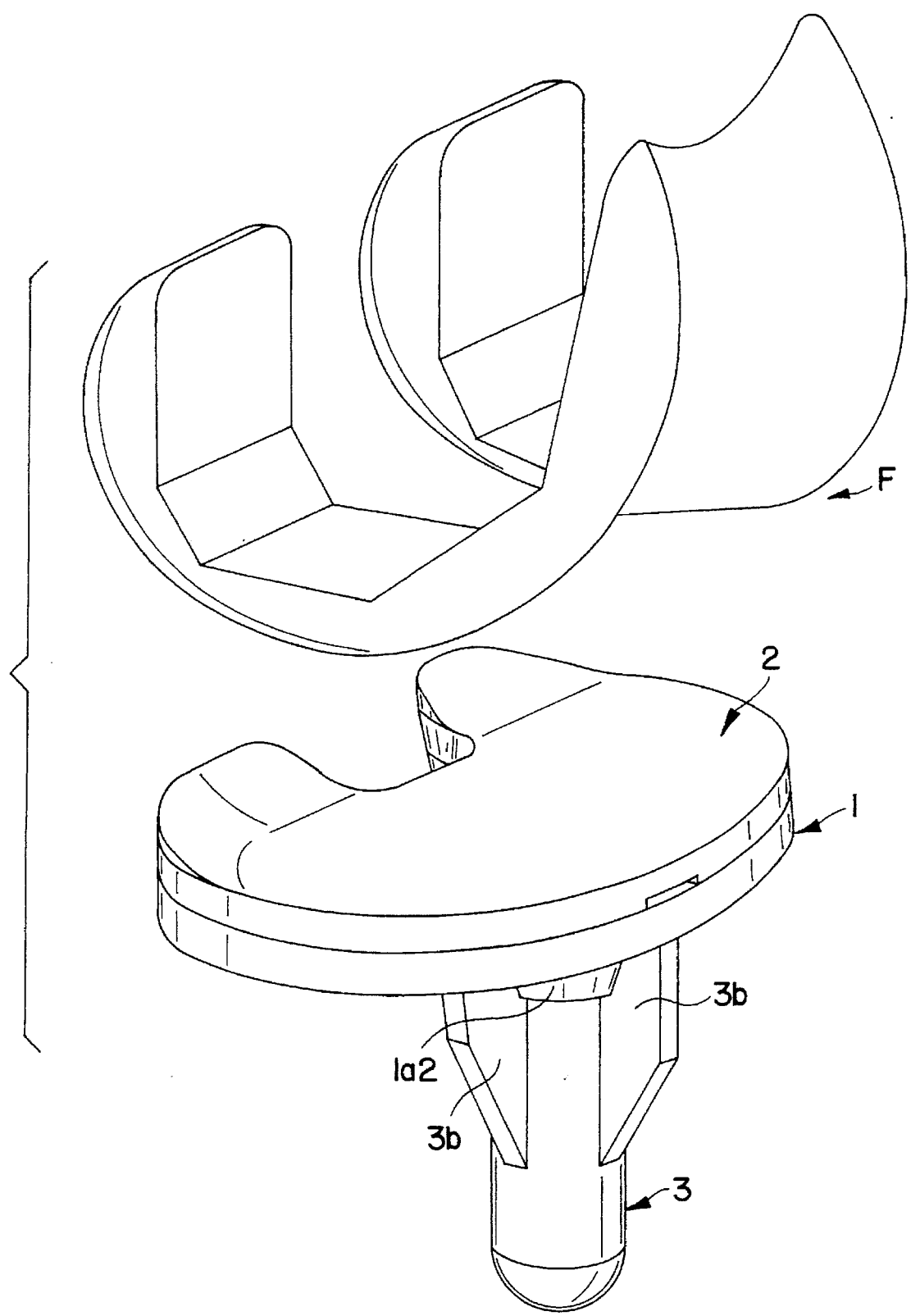
FIG. 2 is a perspective view, corresponding to FIG. 1 after assembly of the components of the tibial implant, which is shown as a three quarters view from above.

The tibial implant comprises a tibial socket (1) accepting a polyethylene tibial plate (2) and a stabilizing and/or anchoring pin (3). The plate (2) of this tibial implant co-operates with all types of femoral implant (F). The tibial socket (1) has an asymmetric shape to take into account the asymmetry existing between the internal and external compartments of the tibial head.

According to the invention, the tibial socket (1) has a traversing recess (1a) shaped so as to allow, from its upper face (1b), the engagement, centering and holding in place of the pin (3).

Figure 3:
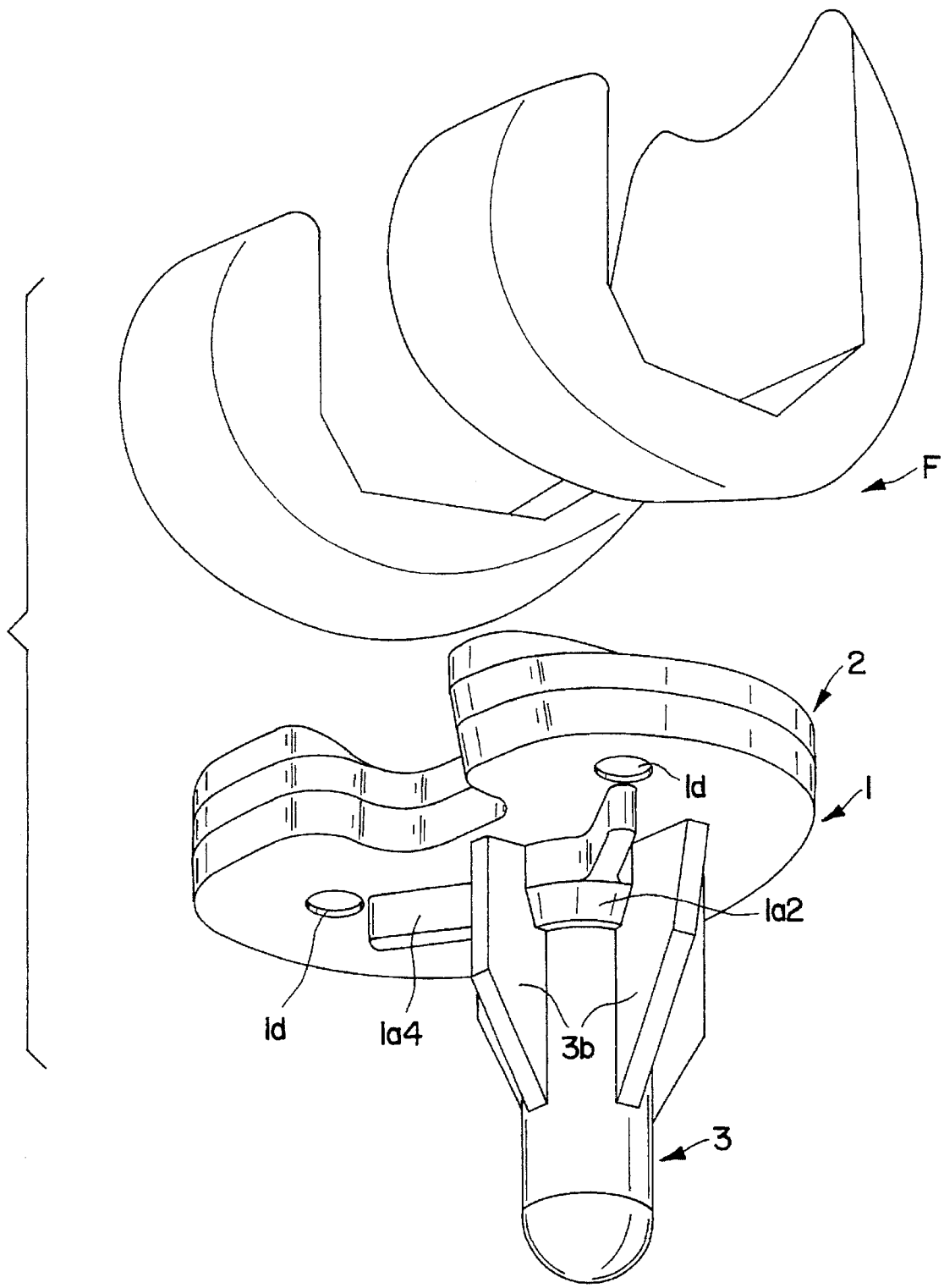
FIG. 3 is a similar view to FIG. 2, with the tibial implant shown in three quarters view from below.

This recess (1a) is extended by a protuberance (1a1) jutting out from the lower face (1c) of the tibial socket (1). This protuberance (1a1) is shaped to act as a stabilizing pin, to ensure, if necessary, the primary fixing of the tibial socket (1). This protuberance (1a1) has a flattened cone-shaped extension (1a2). In addition, this protuberance can be extended laterally by ribs for rigidity (1a4) (FIG. 3).

The recess (1a) has an internal counterboring (1a3) for the centering and support of a head (3a) formed at the upper extremity of the pin (3).

In the example illustrated, the pin (3) has a cylindrical body. In these conditions, the recess (1a) has a corresponding section. In addition, the head (3a) of the pin (3) has vertical slits (3a1) around its periphery. This head delineates a flattened cone-shaped internal counterboring (3a2) opening up in a threaded hole (3b) for the insertion of a screw (4). This screw (4) has a flattened cone shaped head with a section complementary to the counterboring (3a2) such that, during the action of inserting the screw into the pin, the screw causes diametric expansion of the head (3a) of the pin, thereby ensuring its binding to the tibial socket (1).

The pin (3) has, jutting out from its surface line, radial stabilizing fins (3b). The traversing recess (1a) of the tibial socket (1) has slits (1a5), also traversing, whose number and orientation correspond to the number and orientation of the fins (3b) of the pin (3), and thus, cooperate With the fins (3b) during the insertion of the pin (3).

Figure 4:
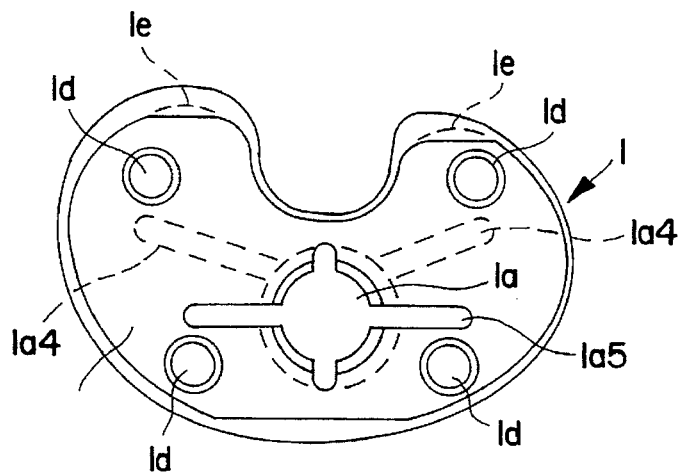
FIG. 4 is a plan view of the tibial socket.
Figure 5:
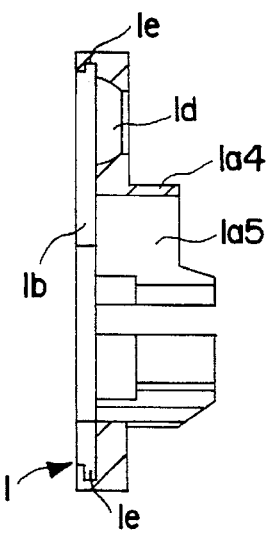
FIG. 5 is a cross section following the line 5.5 of FIG. 4.
Figure 6:
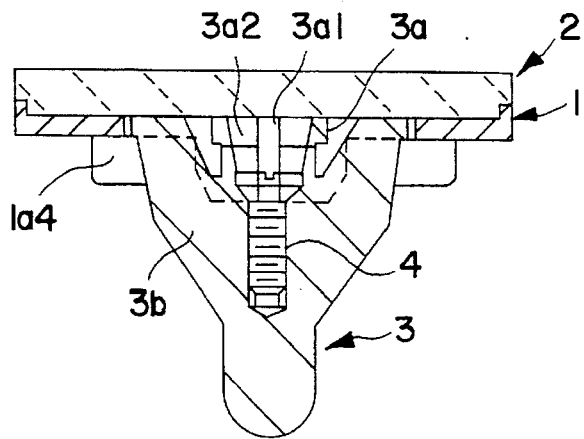
FIG. 6 is a cross section following the line 6.6 in FIG. 4.

The tibial socket (1) also has holes (1d) for the insertion of spongy bone screws (not shown). For example, as shown in FIG. 4, the socket has four holes (1d). These holes are shaped to make it possible to embed the heads of the screws, if necessary permitting their angular orientation.

The technical characteristics of the tibial socket (1) are especially advantageous for its impaction.

Firstly, a doctor positions the socket (1), without the pin. The flattened cone-shaped protuberance (1a1) aids in the primary fixing of said socket, thus permitting perfect periodical support.

Subsequently, the doctor fixes the socket using spongy bone screws inserted in the holes (1d). It is thus possible to introduce the pin through the recess (1a), which also acts as a boring guide. All that remains to be done is the fixing of the pin to the socket, which produces expansion of the head (3a) by means of the screw (4).

It is therefore evident that the introduction of the pin (3) from above the socket (1) allows it to be firmly attached to the said socket after the latter is correctly impacted. The result is that the pin does not interfere with the positioning of the socket and therefore the supports are perfectly respected.

After impaction of the tibial socket and of the pin (3) in the manner described above, the doctor positions the polyethylene plate in the socket (1). For this purpose, the socket (1) has a peripheral rim (1e) shaped for the fixing of the plate (2) mainly by snap-fitting. The shapes and the profiles of the plate (2) are not described because various embodiments are possible. The same applies to the femoral implant (F).

The constitutive parts of the tibial implant, notably the socket (1) and the pin (3), can be of any material and can have any type of surface treatment.

In an alternative embodiment (non-illustrated), the head of the pin and/or the traversing recess (1a) of the socket is equipped with additional means allowing the angular orientation of said pin and its locking in position. For example, these means may comprise a spherical head, situated at the level of the head (3a), intended to be inserted in the opening (1a) of the tibial socket with a complementary spherical shape.

These arrangements prove to be especially advantageous for replacement prostheses for which quite large pins are used. If the pin is perpendicular to the socket (1b) and if the surgeon tilts the socket backwards, the pin makes contact with the anterior cortical area. This possibility of angular adjustment of the pin relative to the socket thus makes it possible to align said pin in the axis of the tibial medullary canal.

The pin (3) can also be covered with a dense, non-osteoconductive, ceramic material whose reabsorption can be controlled by altering the composition of said material.

The advantages are apparent from the description; in particular, the following are emphasized and restated:

placement of the pin after impaction of the tibial socket, taking into account its introduction from the upper face of said socket, avoids adverse effects on the cortical support desired, ease of impaction, possibility of equipping the socket with various pin shapes suited to the pathological case to be treated, orientation of the pin relative to the tibial socket, notably in the case of replacement prostheses.

I claim:

1. A tibial implant for a knee prosthesis comprising:

a tibial socket configured to accept a polyethylene trial plate; and, an elongated pin for anchorage in the bone and for supporting the tibial implant, said pin terminating at opposite ends wherein a head portion is formed at one end, said head portion having radial stabilizing fins extending outwardly from said pin;

said tibial socket having a conical wall with a recess formed therein defining an internal counterbore and slits formed in said wall wherein said socket is configured to receive said head and said stabilizing fins of said pin;

said head having a threaded internal counterbore formed therein for accepting a screw and having vertical slits formed around said counterbore;

said screw having a flattened cone-shaped head with a section that conmmnicates with said internal counterbore such that insertion of the screw into the pin causes diametric expansion of the head which securely and rigidly binds the pin to the tibial socket.

2. The tibial implant of claim 1, wherein the tibial socket further comprises a protuberance projecting from a lower face of said tibial socket at the recess in said tibial socket.

3. The tibial implant of claim 1, wherein the protuberance has a flattened cone-shaped extension.

4. The tibial implant of claim 1, wherein the recess and the head are substantially circular in shape.

5. The tibial implant of claim 1, wherein the tibial socket has through holes to facilitate insertion of spongy bone screws for fixing the tibial socket.

6. The tibial implant of claim 1, wherein the tibial socket has a peripheral rim; wherein the tibial plate has a peripheral collar; and wherein said peripheral rim engages said peripheral collar for snap fitting of said tibial plate to said tibial socket.

* * * * *

UNITED STATES PATENT AND TRADEMARK OFFICE
CERTIFICATE OF CORRECTION

PATENT NO. : 5,658,341
DATED : August 19, 1997
INVENTOR(S) : Jacques Delfosse

It is certified that error appears in the above-indentified patent and that said Letters Patent is hereby corrected as shown below:

Column 3, lines 14-15, delete "periodical" and insert therefor
--pericortical--.

Column 4, line 18, Claim 1, delete "trial" and insert therefor
--tibial--.

Column 4, line 33, Claim 1, delete "conmmunicates" and insert
therefor --communicates--.

Signed and Sealed this

Sixteenth Day of December, 1997

Attest:

BRUCE LEHMAN

Attesting Officer

Commissioner of Patents and Trademarks